(12) United States Patent
Tuffin et al.

(10) Patent No.: US 7,910,018 B2
(45) Date of Patent: Mar. 22, 2011

(54) COMPOUNDS FOR USE IN LIQUID CRYSTAL DEVICES

(75) Inventors: Rachel P Tuffin, Worcester (GB); Stephane Trombotto, Villeurbanne (FR); John W Goodby, York (GB); Michael Hird, Hull (GB)

(73) Assignee: Qinetiq Limited, London (GB)

( * ) Notice: Subject to any disclaimer, the term of this patent is extended or adjusted under 35 U.S.C. 154(b) by 868 days.

(21) Appl. No.: 11/665,765

(22) PCT Filed: Nov. 1, 2005

(86) PCT No.: PCT/GB2005/004204
§ 371 (c)(1),
(2), (4) Date: Apr. 19, 2007

(87) PCT Pub. No.: WO2006/048620
PCT Pub. Date: May 11, 2006

(65) Prior Publication Data
US 2009/0066905 A1       Mar. 12, 2009

(30) Foreign Application Priority Data
Nov. 3, 2004   (GB) .................................. 0424308.5

(51) Int. Cl.
*C09K 19/00*       (2006.01)
*C09K 19/06*       (2006.01)
*C09K 19/52*       (2006.01)
*G02F 1/1333*      (2006.01)

(52) U.S. Cl. ............ 252/299.01; 252/299.6; 252/299.61; 252/299.62; 252/299.63; 430/20; 349/1; 349/182; 428/1.1

(58) Field of Classification Search ............. 252/299.01, 252/299.6–299.63; 430/20; 428/1.1; 349/1, 349/182
See application file for complete search history.

(56) References Cited

U.S. PATENT DOCUMENTS
4,462,923 A    7/1984   Boller et al.
4,734,217 A    3/1988   Demus et al.

FOREIGN PATENT DOCUMENTS
DE    33 35 244      4/1985
DE    199 21 318    11/1999
JP    2007-13561     1/2007

OTHER PUBLICATIONS
International Search Report for PCT/GB2005/004204 mailed Apr. 18, 2006.

*Primary Examiner* — Geraldina Visconti
(74) *Attorney, Agent, or Firm* — Nixon & Vanderhye P.C.

(57) ABSTRACT

Liquid crystal compounds of Formula (I) for use in liquid crystal devices contains a dioxatetralin unit within the mesogenic liquid crystal core. The dioxatetralin unit may be located at any position within the mesogenic core of the liquid crystal compound, either at the terminus of the liquid crystal core or alternatively substantially in the middle of the liquid crystal core. The compounds of the invention exhibit fast switching and may be used in liquid crystal mixtures for particular use in imaging or display media, such as monitors or televisions.

32 Claims, 1 Drawing Sheet

COMPOUNDS FOR USE IN LIQUID CRYSTAL DEVICES

This application is the U.S. national phase of international application PCT/GB2005/004204 filed 1 Nov. 2005, which designated the U.S. and claims benefit of GB 0424308.5 filed 3 Nov. 2004, the entire contents of each of which are hereby incorporated by reference.

The present invention relates to novel compounds which are useful in the context of liquid crystal devices, either as liquid crystal compounds or as components of liquid crystal mixtures. The present invention also relates to processes for preparing such novel compounds and to liquid crystal mixtures or devices containing such compounds.

The phrase "liquid crystals" is well known. It refers to compounds which, as a result of their structure, have a phase or phases intermediate between liquid and solid and which are characterised by orientational ordering and a decrease in positional ordering, preferably at working temperatures for example, of from −40 to 200° C. These materials are useful in various devices, in particular in liquid crystal display devices.

Liquid crystals can exist in various phases. In essence there are three different classes of liquid crystalline material, each possessing a characteristic molecular arrangement. Those classes are nematic, chiral nematic (cholesteric) and smectic. For a fuller description of liquid crystal phases and devices see for example "The Handbook of Liquid Crystals", Ed D Demus, J Goodby, G W Gray, H-W Spiess, V Vill, Pub Wiley VCH, 1998.

Broadly speaking, the molecules of nematic compounds will align themselves in a particular orientation in a bulk material. Smectic materials, in addition to being orientated in a similar way, will align themselves closely in layers.

A wide range of smectic phases exists for example, smectic A and smectic C. In the former, the molecules are aligned perpendicularly to a base or support, whilst in the latter, molecules may be inclined to the support. Some liquid crystal materials possess a number of liquid crystal phases upon varying the temperature. Others have just one phase. For example, a liquid crystal material may show the following phases on being cooled from the isotropic phase: —isotropic—nematic—smectic A—smectic C—solid. If a material is described as being smectic A then it means that the material possesses a smectic A phase over a useful working temperature range.

Such materials are useful, in particular, in display devices where their ability to align themselves and to change their alignment under the influence of voltage, is used to impact on the path of polarised light, thus giving rise to liquid crystal displays. These are widely used in devices such as watches, calculators, display boards or hoardings, televisions and computer screens, in particular, laptop computer screens etc. The properties of the compounds which impact on the speed with which the compounds respond to voltage charges include molecule size, conductivity, viscosity, dielectric anisotropy ($\Delta\in$) or dipole moment ($\mu$) and in the smectic C phase the spontaneous polarisation, etc. Alternatively the light may be unpolarised and a dichroic dye may be incorporated into the mixture to give a change in the optical properties on switching of the device, (Guest-host LCD).

The properties of these compounds vary depending upon their structure. Therefore, various different structures are useful in establishing a wide range of different properties which can then be specifically matched to the target application. For example, compounds with low birefringence ($\Delta n \sim 0.12$), such as some phenylcyclohexyl derivatives, have practical application in devices that use a reflective light mode of operation, whereas mixtures with a high birefringence allow the use of much thinner devices or transmissive mode.

The applicants have devised a novel series of compounds which contain a dioxatetralin moiety which compounds possess useful properties for use as liquid crystals materials.

According to the present invention, there is provided a compound of Formula (I)

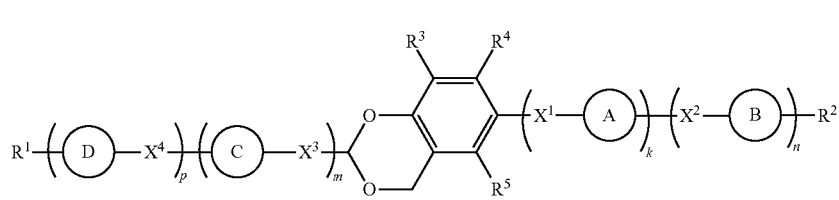

(I)

wherein $R^1$ and $R^2$ are independently selected from cyano, halo, optionally substituted hydrocarbyl, optionally substituted alkoxy, optionally substituted heterocyclyl, a group $R^{13}C(O)O$— or $R^{13}OC(O)$— where $R^{13}$ is optionally substituted hydrocarbyl;

$R^3$, $R^4$ and $R^5$ are independently selected from hydrogen, halogen, $CF_3$ or $SF_5$;

$X^1$, $X^2$, $X^3$ and $X^4$ are independently selected from a direct bond, —$CH_2CH_2$—, —$(CH_2)_4$—, —$CH_2O$—, —$CH=CH$—, —$C\equiv C$—, —$COO$—, —$OCO$—, or —$OCH_2$—;

and A, B, C and D are independently selected from a 1,4-phenylene, 1,4-cyclohexyl or a heterocyclic ring, any of which may be optionally substituted;

and n is 0 or 1, m is 0 or 1, p is 0 or 1 and k is 0 or 1, provided that k+m+n+p is greater than 0, further provided that if k is 0 then n is 0, and also provided that if m is 0 then p is 0.

As used herein, the term "hydrocarbyl" refers to any structure comprising carbon and hydrogen atoms. For example, these may be alkyl, alkenyl, alkynyl, aryl such as phenyl or napthyl, arylalkyl, cycloalkyl, cycloalkenyl or cycloalkynyl. Suitably they will contain up to 20 and preferably up to 10 carbon atoms.

The term "heterocyclic" includes aromatic or non-aromatic rings, for example containing from 4 to 20, suitably from 5 to 10 ring atoms, at least one of which is a heteroatom such as oxygen, sulphur or nitrogen. Examples of such groups include furyl, thienyl, pyrrolyl, pyrrolidinyl, imidazolyl, triazolyl, thiazolyl, tetrazolyl, oxazolyl, isoxazolyl, pyrazolyl, pyridyl, pyrimidinyl, pyrazinyl, pyridazinyl, triazinyl, quinolinyl, isoquinolinyl, quinoxalinyl, benzthiazolyl, benzoxazolyl, benzothienyl or benzofuryl.

As used herein, the term "alkyl" refers to straight or branched chain alkyl groups, suitably containing up to 20 and preferably up to 6 carbon atoms, and the term "alkoxy" relates to —O-alkyl groups. The term "alkenyl" and "alkynyl" refer to unsaturated straight or branched chains which include for example from 2-20 carbon atoms, for example from 2 to 6 carbon atoms. In addition, the term "aryl" refers to aromatic groups such as phenyl or naphthyl. The terms "cycloalkyl", "cycloalkenyl" and "cycloalkynyl" refer to such groups which are cyclic and have at least 3 and suitably from 5 to 20 ring atoms. These rings may be fused together to form bicyclic, tricyclic or even larger multiple ring systems.

Optionally substituted hydrocarbyl groups may be substituted by functional groups, or by other types of hydrocarbyl group. For example, cyclic groups such as aryl, heterocyclic or cycloalkyl, cycloakenyl or cycloalkynyl, any of which may be substituted by hydrocarbyl chains such as alkyl, alkenyl or alkynyl groups as well as functional groups. Where the hydrocarbyl group is itself an alkyl, alkenyl or alkynyl group, it may be substituted with cyclic groups such as heterocyclic groups, aryl groups, cycloalkyl, cycloalkenyl or cycloalkynyl groups, as described above, which may themselves be further substituted by hydrocarbyl or functional groups. Optionally substituted hydrocarbyl may also have one or more non-adjacent carbon atoms replaced by O, S, $CO_2$, or OCO or $C\equiv C$—.

The term "functional group" refers to reactive groups such as halo, cyano, nitro, oxo, $C(O)OR^a$, $C(O)R^a$, $OC(O)R^a$, $OR^a$, $S(O)_tR^a$, $NR^bR^c$, $OC(O)NR^bR^c$, $C(O)NR^bR^c$, —$NR^bC(O)OR^a$, —$NR^bC(O)R^a$, —$NR^aCONR^bR^c$, =$NOR^a$, —$N\!\!=\!\!CR^bR^c$, $S(O)_tNR^bR^c$ or —$NR^bS(O)_tR^a$ where $R^a$, $R^b$ and $R^c$ are independently selected from hydrogen or optionally substituted hydrocarbyl, or $R^b$ and $R^c$ together form an optionally substituted ring which optionally contains further heteroatoms such as sulphur, S(O), $S(O)_2$, oxygen and nitrogen, t is 0 or an integer of from 1-3.

The term "heteroatom" as used herein refers to non-carbon atoms such as oxygen, nitrogen, selenium or sulphur atoms as mentioned above. Where the nitrogen atoms are present, they may be present as part of an amino residue such that they will be substituted for example by hydrogen or alkyl.

Conveniently, when present hydrocarbyl groups may be substituted by alkyl, alkoxy or halogen.

In the above defined liquid crystal compound, groups $R^1$ and $R^2$ represent suitable terminal end groups, while the remaining interposed structure represents the mesogenic core.

Usually $R^1$ and $R^2$ will not comprise further ring systems (to those of A, B, C or D); in particular $R^1$ and $R^2$ will not usually be selected from an optionally substituted 1,4-phenylene, 1,4-cyclohexyl or a heterocyclic ring.

When $R^1$ and $R^2$ are alkyl or alkoxy groups, they suitably have from 3 to 8 carbon atoms, and preferably have from 3 to 5 carbon atoms. Suitably these carbon atoms are arranged in a straight chain.

Preferably $R^1$ and $R^2$ are independently selected from alkyl or alkoxy. For most arrangements the adjacent atom to the acetal group (which atom may form part of $R^1$, (where p=m=0) or part of $X^3$) will not be selected from a heteroatom which causes the acetal functionality to become labile. Thus, when p=m=0, $R^1$ is preferably alkyl and not alkoxy.

Substitution directly upon the dioxatetralin moiety is advantageous because the substituted atoms are locked in position relative to the oxygens of the acetal moiety. Preferably, at least one of $R^3$, $R^4$ and $R^5$ is halogen. Where any of $R^3$, $R^4$ or $R^5$ is halogen, they are suitably fluorine or chlorine, but are preferably fluorine. Thus in particular, $R^3$, $R^4$ and $R^5$ are selected from hydrogen or fluorine.

$X^1$ and $X^3$ are preferably independently selected from a direct bond, —$CH_2CH_2$—, —$(CH_2)_4$—, —$CH_2O$—, —CH=CH—, or —C≡C—.

Suitably, $X^1$, $X^2$, $X^3$ and $X^4$ are selected from a direct bond or a group —$CH_2CH_2$—. Preferably no more than one of $X^1$, $X^2$, $X^3$ and $X^4$ is a group —$CH_2CH_2$— and most preferably $X^1$, $X^2$, $X^3$ and $X^4$ are all direct bonds. Preferably $X^3$ is not directly attached by an oxygen atom. In a preferred option when m+p=0 and $R^1$ is alkyl then $X^1$ may not be —COO—.

Preferably k+m+n+p is less than or equal to 3, preferably k+m+n+p is 1 or 2.

It is within the scope of the invention that the dioxatetralin unit may be located at any position within the liquid crystal compound, that is to say it may be at either end of the liquid crystal core or alternatively substantially in the middle of the liquid crystal core.

Advantageously, rings A, B, C or D are selected from 1,4-phenylene, 1,4-cyclohexyl, 2,5-dioxanyl, pyridyl or 2,5-pyrimidinyl. Preferably A, B, C and/or D are all 1,4-phenylene or, inner rings A or C when present are 1,4-phenylene and outer rings B or D, when present are 1,4-cyclohexyl. More preferably, when present A, B, C, and D are 1,4-phenylene or optionally substituted 1,4-phenylene.

Preferred optional substituents for rings A, B, C, and D are halo and in particular fluoro, and advantageously, all substituents on these rings are fluoro. Preferably, at least one ring of A, B, C, and D, when present, includes two fluoro substituents arranged on adjacent carbon atoms within that ring.

In a particularly preferred embodiment, at least one further ring selected from A or B or C or D, when present, also includes at least one fluoro substituent, and advantageously if the structure is conformationally locked and/or not free to rotate, all fluorine atoms, which are present, are on the same side of the structure.

Usually, the compound of Formula (I) will contain at least one fluorine atom, either disposed on the dioxatetralin unit or more usually substituted on one of the rings, A, B, C or D. Preferably, the compound of Formula (I) will contain 2 or more fluorine atoms, and even more preferably the compound of Formula (I) will contain 3 or more fluorine atoms.

The use of lateral fluoro-substitution of the rings, imparts strong lateral dipolar properties resulting in the materials exhibiting negative dielectric anisotropy in the nematic phase. The incorporation of at least three fluoro substituents generally provides a particularly strong negative dielectric anisotropy and in the smectic C phase increases the dielectric biaxiality. The fluoro substituents may be present on any one of rings A, B, C, D and/or the dioxatetralin unit, and the substitution may be on adjacent rings or on non-adjacent rings. Any cyclohexyl rings present are preferably not substituted, however if the cyclohexyl rings are substituted with at least one fluorine atom, care must be taken to avoid the loss of hydrogen fluoride.

The appropriate selection of the degree of fluorination (if any), and/or when present the substitution pattern of the fluorination, results in compounds of Formula (I) which may provide liquid crystals which are suitable for use in a number of modes such as: positive dielectric anisotropy nematics (AM/TN/STN), negative dielectric anisotropy nematics (VA mode) and smectics, such as ferroelectric, antiferroelectic and electroclinic devices.

Negative dielectric anisotropy nematic liquid crystals are of particular use in vertically aligned (VA) mode liquid crystal devices used mainly for display including television display applications. There are a number of embodiments of VA LCD but all require liquid crystal mixtures exhibiting negative dielectric anisotropy.

The liquid crystal compounds of Formula (I) are non-linear or bent; one of the advantages is that it may lead to compounds exhibiting lower melting points.

The compounds of Formula (I) are chiral and they may be used to form chiral phases, examples of which are smectic C* or cholesteric phases. Preferably, the compounds may be formed as a racemic mixture and the resulting racemate used as a non-optically active liquid crystal compound and or mixture.

Useful compounds, in which rings C and D are not present, comprise a compound of Formula (XIX)

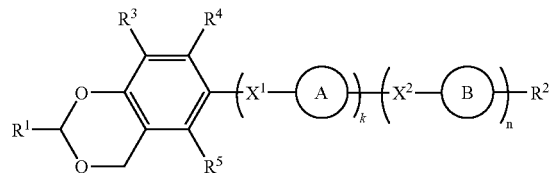

(XIX)

where k, n, $R^1$, $R^2$, $R^3$, $R^4$, $R^5$, $X^1$, $X^2$, A and B are as defined above, and k+n>0.

In the case of an electro-optic device based upon ferroelectric switching of a tilted chiral smectic liquid crystal turnaround enhances the reduction in the switching voltage, which is exhibited as the $\tau V_{min}$ the switching curve. Perfluorinated compounds of Formula (I) where any three of the hydrogens in any of rings A, B, C and D when present, are substituted with fluorine, may exhibit turnaround.

In a preferred embodiment, the invention provides a compound of Formula (II)

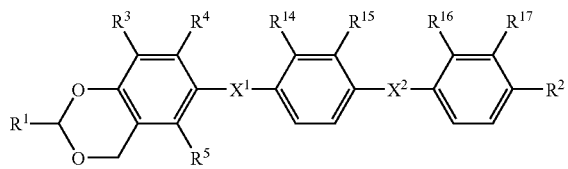

(II)

where $R^1$, $R^2$, $R^3$, $R^4$, $R^5$, $X^1$ and $X^2$ are as defined above, and $R^{14}$, $R^{15}$, $R^{16}$ and $R^{17}$ are independently selected from hydrogen or halogen and in particular from fluorine. Individual groups $X^1$ and $X^2$ may be the same or different.

In a particular embodiment, one, two or three of $R^3$, $R^4$, $R^5$, $R^{14}$, $R^{15}$, $R^{16}$ and $R^{17}$ are fluorine and the others are hydrogen. Where any three are fluorine, as indicated above, turnaround may be exhibited.

The use of at least three fluoro substituents in the compounds of Formula (I) and derivatives hereinafter defined also have a tendency to reduce the melting points of the compounds.

The compounds of Formula (II) are particularly suitable for use as additives to mixtures of compounds which require high smectic C phase stability wherein only 2 of $R^3$, $R^4$, $R^5$, $R^{14}$, $R^{15}$, $R^{16}$ and $R^{17}$ are fluoro and the others are hydrogen.

Particularly preferred examples of liquid crystal compounds of Formula (II) are listed in the following Table 1.

TABLE 1

| Ref No. | $R^3$ | $R^4$ | $R^5$ | $R^{14}$ | $R^{15}$ | $R^{16}$ | $R^{17}$ | $R^2$ |
|---|---|---|---|---|---|---|---|---|
| 1 | H | H | H | H | H | H | H | $C_5H_{11}$ |
| 2 | H | H | H | H | H | H | H | $OC_5H_{11}$ |
| 3 | H | H | H | H | F | H | H | $C_5H_{11}$ |
| 4 | H | H | H | H | F | H | H | $OC_5H_{11}$ |
| 5 | H | H | H | F | H | H | H | $C_5H_{11}$ |
| 6 | H | H | H | F | H | H | H | $OC_5H_{11}$ |
| 7 | H | H | H | F | F | H | H | $C_5H_{11}$ |
| 8 | H | H | H | F | F | H | H | $OC_5H_{11}$ |
| 9 | H | F | H | H | F | H | H | $C_5H_{11}$ |
| 10 | H | F | H | H | F | H | H | $OC_5H_{11}$ |
| 11 | F | H | H | F | H | H | H | $C_5H_{11}$ |
| 12 | F | H | H | F | H | H | H | $OC_5H_{11}$ |
| 13 | H | F | H | F | F | H | H | $C_5H_{11}$ |
| 14 | H | F | H | F | F | H | H | $OC_5H_{11}$ |
| 15 | F | H | H | F | F | H | H | $C_5H_{11}$ |
| 16 | F | H | H | F | F | H | H | $OC_5H_{11}$ |

Particular examples of liquid crystal compounds of Formula (III) are listed in the following Table 2.

TABLE 2

| No. | $R^3$ | $R^4$ | $R^5$ | $R^{14}$ | $R^{15}$ | $R^2$ |
|---|---|---|---|---|---|---|
| 33 | H | H | H | H | H | $C_5H_{11}$ |
| 34 | H | H | H | H | H | $OC_5H_{11}$ |
| 35 | H | H | H | H | F | $C_5H_{11}$ |
| 36 | H | H | H | H | F | $OC_5H_{11}$ |
| 37 | H | H | H | F | H | $C_5H_{11}$ |
| 38 | H | H | H | F | H | $OC_5H_{11}$ |
| 39 | H | H | H | F | F | $C_5H_{11}$ |
| 40 | H | H | H | F | F | $OC_5H_{11}$ |
| 41 | H | F | H | H | F | $C_5H_{11}$ |
| 42 | H | F | H | H | F | $OC_5H_{11}$ |
| 43 | F | H | H | F | H | $C_5H_{11}$ |
| 44 | F | H | H | F | H | $OC_5H_{11}$ |
| 45 | H | F | H | F | F | $C_5H_{11}$ |
| 46 | H | F | H | F | F | $OC_5H_{11}$ |
| 47 | F | H | H | F | F | $C_5H_{11}$ |
| 48 | F | H | H | F | F | $OC_5H_{11}$ |

The compounds of the invention, and, in particular those in Tables 1 and 2, may form nematic and/or smectic phases and are useful as liquid crystal compounds.

When rings C and D are not present and when B is a 1,4-cyclohexyl group, it is preferably unsubstituted. Thus, in an alternative preferred embodiment, a compound of Formula (III)

(III)

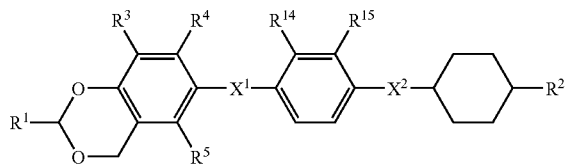

where $R^1$, $R^2$, $R^3$, $R^4$, $R^5$, $R^{14}$, $R^{15}$, $X^1$ and $X^2$ are as defined above.

Preferred compounds of Formula (XIX), where ring B is absent, include compounds of Formula (X), (X)

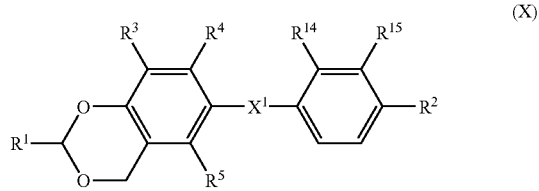

where $R^1$, $R^2$, $R^3$, $R^4$, $R^5$, $X^1$, $R^{14}$ and $R^{15}$ are as previously defined. Preferably two or three of $R^3$, $R^4$, $R^5$, $R^{14}$ and $R^{15}$ are fluorine and the others are hydrogen.

In a further preferred embodiment, m is 1 and k is 1, both p and n are 0, and there is a ring either side of the dioxatetralin unit, providing a compound of Formula (XX), (XX)

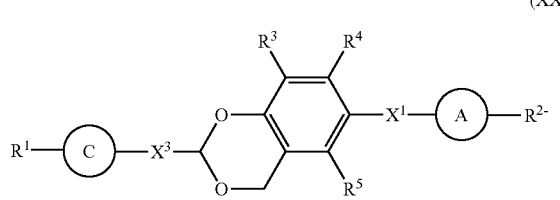

where $R^1$, $R^2$, $R^3$, $R^4$, $R^5$, $X^1$, $X^3$, A and C are as hereinbefore defined.

Preferably, either ring A or ring C, or ideally both rings are substituted by at least one fluorine atom. Usually, 2 or more fluorine atoms will be present in this compound.

Conveniently, when n and p are 0, and both m and k are 1, a preferred compound of Formula (XX), provides compound of Formula (XV), (XV)

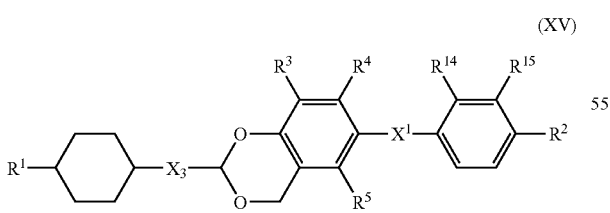

where $X^1$ and $X^3$ are as previously defined and $R^1$, $R^2$, $R^3$, $R^1$, $R^5$, $R^{14}$ and $R^{35}$ are as previously defined, and may be independently selected from hydrogen or halogen. Preferably one, two or three of $R^3$, $R^4$, $R^5$, $R^{14}$ and $R^{15}$ are fluorine and the others are hydrogen. The alternative where A is selected from cyclohexyl and C is 1,4-phenylene may also be suitably prepared.

Conveniently, a compound of Formula (XXV) may be provided, (XXV)

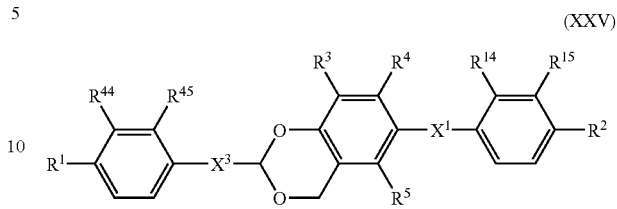

where $R^1$, $R^2$, $R^3$, $R^4$, $R^5$, $X^1$ and $X^3$ are as hereinbefore defined, and $R^{14}$, $R^{15}$, $R^{44}$ and $R^{45}$ are independently selected from hydrogen or halogen.

In a yet further embodiment, where n is 0 and k is 0, at least one ring may be provided on the acetal part of the dioxane-tetralin unit, providing the liquid crystal with a bulky end group, and thereby providing a compound of Formula (XVIII), (XVIII)

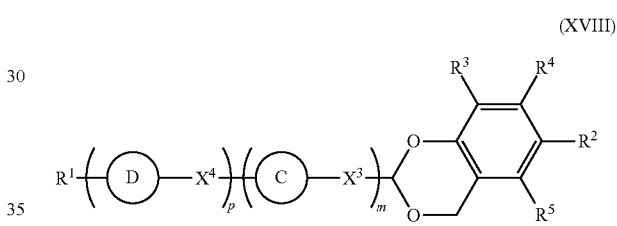

where p, m, $R^1$, $R^2$, $R^3$, $R^4$, $R^5$, $X^3$, $X^4$, C and D are as hereinbefore defined.

Rings C or D may be substituted by at least one fluorine atom and 2 or more of then may be present.

A preferred compound of Formula (XVIII), may be provided by Formula (XXX), (XXX)

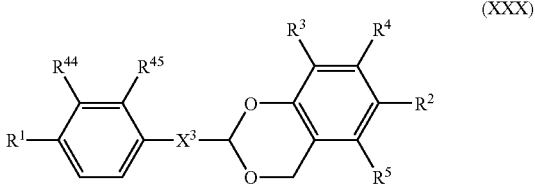

where $R^1$, $R^2$, $R^3$, $R^4$, $R^5$, $X^3$ are as hereinbefore defined, and $R^{44}$ and $R^{45}$ are independently selected from hydrogen or halogen; preferably the halogen is fluorine. Preferably one, two or three of $R^3$, $R^4$, $R^5$, $R^{44}$ and $R^{45}$ are fluorine and the others are hydrogen.

Conveniently, a further preferred compound of Formula (XVIII) may be provided by a compound of Formula (XXXV), (XXXV)

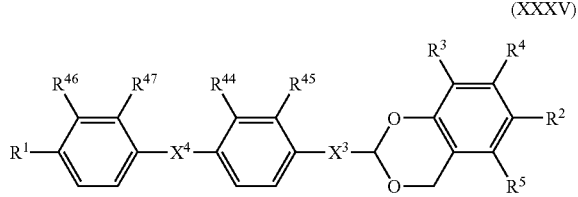

where $R^1$, $R^2$, $R^3$, $R^4$, $R^5$, $X^3$ and $X^4$ are as hereinbefore defined and $R^{44}$, $R^{45}$, $R^{46}$ and $R^{47}$ are independently selected from hydrogen or halogen, preferably the halogen is fluorine. Preferably at least one, two or three of $R^3$, $R^4$, $R^5$, $R^{44}$, $R^{45}$, $R^{46}$ and $R^{47}$ are fluorine and the others are hydrogen.

The compounds of the invention are generally chemically and photochemically stable, and exhibit high resistivities.

The materials of the invention may be able to align in the nematic phase in either homeotropic or planar orientation as required depending on the surface treatment of the device.

Single liquid crystal materials are unlikely to show all the properties required of the liquid crystal material present in a device, thus mixtures comprising one or more compounds of Formula (I), or, mixing with other known liquid crystal compounds may be necessary to achieve the desired results. It is important that the compounds remain in solution with each other: this is a particular problem in smectic C mixtures.

Compounds of the invention show increased miscibility with other liquid crystal compounds, which provides a greater flexibility in mixture formulation.

The compounds of Formula (I) may be suitably prepared by reacting such as, for example, condensing together a compound of Formula (IV)

(IV)

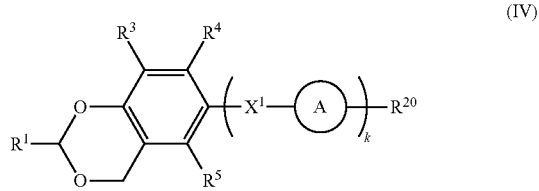

where $R^1$, $R^3$, $R^4$, $R^5$, $X^1$ and A are as defined in relation to Formula (I), k is 1, and $R^{20}$ is a reactive group, such as, for example, boronic acid $B(OH)_2$ or a leaving group, such as, for example, halo, and in particular, a bromide or a group $OSO_2CF_3$, with a compound of Formula (V)

(V)

wherein n, $X^2$, B and $R^2$ are as defined in relation to Formula (I) and $R^{21}$ is a leaving group, such as, for example, halo, and in particular, a bromide or a group $OSO_2CF_3$ where $R^{20}$ is a reactive group, or $R^{21}$ is a reactive group, such as, for example, boronic acid $B(OH)_2$ where $R^{20}$ is a leaving group.

The reaction is suitably effected in the presence of a coupling agent, an organic solvent and a base, an example of which may be $Pd(PPh_3)_4$, in dimethoxyethane (DME) and in the presence of an alkali metal carbonate, such as $Na_2CO_3$.

Compounds of Formula (IV) are novel compounds and so form a further aspect of the invention. They may themselves have liquid crystal properties and so be useful in liquid crystal mixtures, as liquid crystal components, or as dopants or additives.

Compounds of Formula (IV) are suitably prepared, by reacting together a compound of Formula (VI)

(VI)

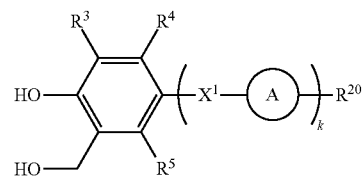

where k, $R^3$, $R^4$, $R^5$, $X^1$ and A, are as defined in relation to Formula (I), with a compound of Formula (VIII), (VIII)

wherein C, D, m, p, $X^3$ and $X^4$ are as hereinbefore defined and wherein $R^{23}$ may be any suitable leaving group, capable of forming an acetal with a diol, compound of the type (VI). Preferably $R^{23}$ is selected from carbonyl or di-halo, more preferably carbonyl.

Conveniently, in Formula (VIII), either 1 or 2 rings may be present, either ring C or rings C and D may be present.

Compounds of Formula (VI) are suitably prepared by reacting together a compound of Formula (VII), (VII)

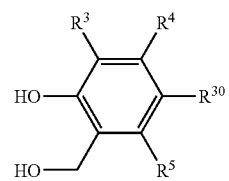

where $R^3$, $R^4$ and $R^5$, are as defined in relation to Formula (I) and $R^{30}$ is a reactive group, such as, for example, boronic acid $B(OH)_2$ or a leaving group, such as, for example, halo, and in particular bromide or a group $OSO_2CF_3$, with a compound of Formula (VIII), (VIIII)

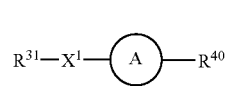

wherein $X^1$ and A are as hereinbefore defined in relation to Formula (I) and $R^{31}$ is a leaving group, such as, for example, halo, and in particular bromide or a group $OSO_2CF_3$ where $R^{30}$ is a reactive group, or $R^{31}$ is a reactive group, such as, for example, boronic acid $B(OH)_2$ where $R^{30}$ is a leaving group, and $R^{40}$ is a leaving group, or a precursor to a leaving group, or a protected leaving group, or is $R^{20}$ or $R^2$, provided that if $R^{40}$ is a leaving group then $R^{31}$ reacts with $R^{30}$ in preference to $R^{40}$.

As indicated above, one or more fluorine atoms may be inserted onto any one or more of the rings A, B, C, D, or the dioxatetralin ring, and this may be undertaken by any convenient fluorination technique.

The invention further provides a novel feature or any combination of novel features as identified above. In a further aspect, the invention provides any compound that is suitable for use as a liquid crystal compound and which has formula (I) as defined above, except that $R^1$ and $R^2$ may be replaced by any terminal end groups commonly used as end groups in liquid crystal compounds.

In a further aspect, the invention provides a liquid crystal mixture comprising at least one compound as described above. Suitably, a liquid crystal mixture may comprise at least two different compounds according to the invention, which are of Formula (I), and optionally other liquid crystal compounds.

In a further aspect of the invention there is provided the use of a compound according to the invention as a liquid crystal compound.

A method of using a liquid crystal compound is also provided, said method comprising selecting a starting material which comprises a compound Formula I and incorporating it in a liquid crystal device.

Compounds of the invention may have application in liquid crystal devices, and one, convenient mode is the use in a reflective light mode of operation. They may also be suitable for applications in liquid crystal on silicon (LcoS) devices and also in twisted nematic (for positive dielectric anisotropy materials) and vertically aligned nematic (VAN) devices (for negative dielectric anisotropy materials). In addition, they may be useful in ferroelectric displays and in STN, Active matrix, or TN devices operating with positive dielectric anisotropy.

The invention also provides a liquid crystal device comprising at least one compound of Formula (I) as described above, or a liquid crystal mixture also as described above.

Conveniently a further aspect of the invention provides a device comprising two spaced cell walls each bearing electrode structures and treated on at least one facing surface with an alignment layer, a layer of a liquid crystal material enclosed between the cell walls, characterised in that it comprises at least one of the compounds according to the current invention.

Further, there is provided a device comprising two spaced cell walls each bearing electrode structures and treated on at least one facing surface with an alignment layer, a layer of a liquid crystal mixture enclosed between the cell walls, characterised in that it incorporates a liquid crystal mixture of at least two compounds according to the current invention.

In an alternative arrangement a device contains cell walls which comprise at least 4 electrodes such as to allow said liquid crystal compound or mixture to be switched in more than one direction.

Further provided is a bistable nematic liquid crystal device comprising;

two cell walls enclosing a layer of liquid crystal material or a mixture (as hereinbefore defined);

electrode structures on both walls;

a surface alignment on the facing surfaces of both cell walls providing alignment to liquid crystal molecules;

means for distinguishing between switched states of the liquid crystal material;

a surface alignment grating on at least one cell wall that permits the liquid crystal molecules to adopt two different pretilt angles in the same azimuthal plane;

the arrangement being such that two stable liquid crystal molecular configurations can exist after suitable electrical signals have been applied to the electrodes;

wherein the layer of liquid crystal material comprises a compound of Formula (I).

The invention will now be described by way of example only, with reference to the following Examples and drawings, in which.

Figure 1:
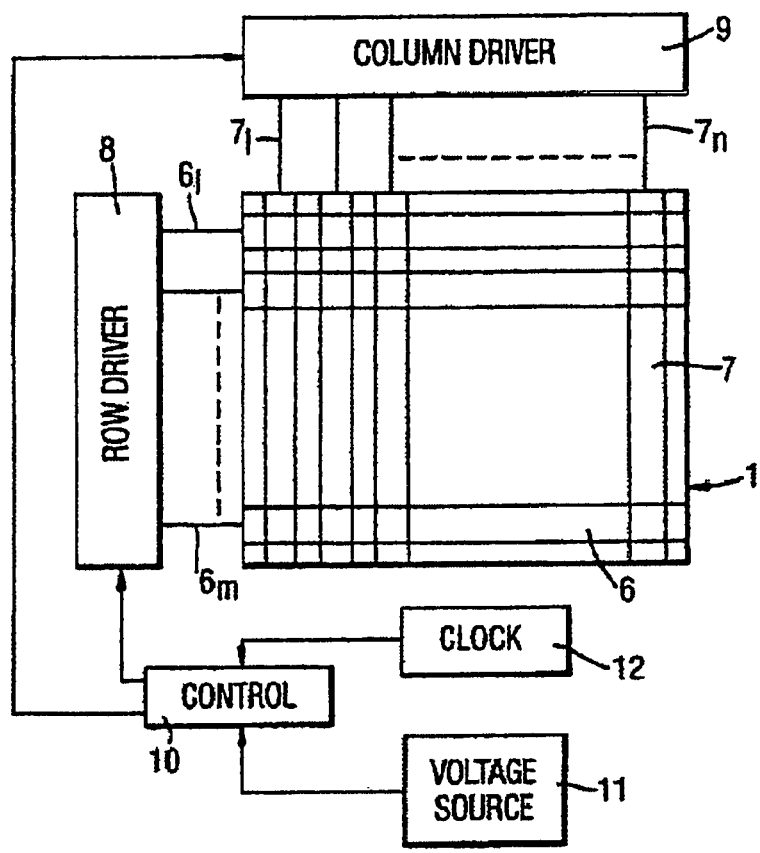
FIG. 1 is a plan view of a matrix multiplex addressed liquid crystal device.
Figure 2:
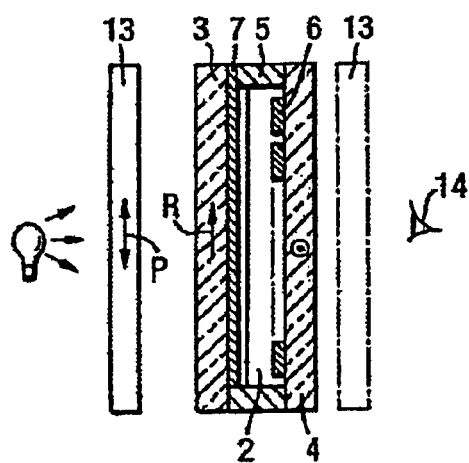
FIG. 2 is a cross-sectional view of the device of FIG. 1 operating in a transmissive mode.
Figure 3:
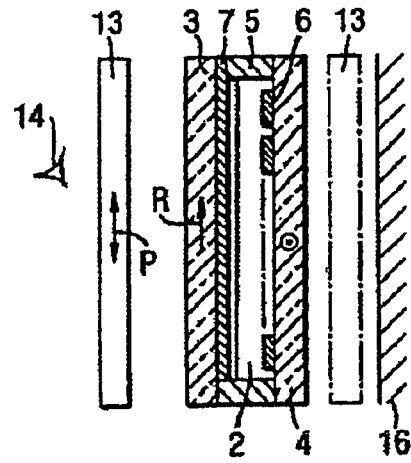
FIG. 3 is similar to FIG. 2, but shows the device operating in a reflective mode.

The device of FIGS. 1, 2 and 3 comprises a liquid crystal cell 1 formed by a layer of a liquid crystal mixture 2, according to the invention contained between two glass walls 3, 4 spaced typically 1 to 15 μm apart by a spacer ring 5. The inside faces of both walls 3, 4 are coated with electrodes 6. The electrodes may be of sheet like form covering the complete wall, or formed, into for example, strip electrodes to provide an array of addressable electrode intersections. The walls are also coated with an aligning layer (not shown) of material according to the current invention.

If the mixture 2 is nematic, then the device may be the known super twisted nematic device, also known as a STN device. In this case, polarisers 13 are used to distinguish between the device voltage ON and OFF states.

The liquid crystal mixture may be a nematic, chiral nematic (cholesteric), or smectic (e.g., ferroelectric) mixture. The device may be used as a display device, e.g., displaying alpha numeric information, or an x, y matrix displaying information. Alternatively, the device may operate as a shutter to modulate light transmission, e.g., as a spatial light modulator, or as a privacy window.

For passive matrix devices (as shown in FIG. 1) strip like row electrodes $6_1$ to $6_m$, e.g. of $InSnO_2$ are formed on one wall 3 and similar column electrodes $7_1$ to $7_n$ are formed on the other wall 4. With m-row electrodes and n-column electrodes this forms an m×n matrix of addressable elements. Each element is formed by the interaction of a row and column electrode. For active matrix devices a discrete nonlinear device eg a transistor or diode is associated with each pixel.

For the passive matrix device a row driver supplies voltage to each row electrode 6. Similarly a column driver 9 supplies voltage to each column electrode 7. Control of the applied voltages is from a control logic 10 which receives power from a voltage source 11 and timing from a clock 12.

For an active device e.g., a thin film transistor active matrix liquid crystal device (TFT AMLCD) three types of electrodes are present, pixel, scanning and signal electrodes as well as a common electrode on the opposite side of the liquid crystal. The control electrode operates the gate such that the voltage on the signal electrode is applied to the relevant pixel electrode.

An example of the use of a mixture and device embodying the present invention will now be described with reference to FIG. 2.

The liquid crystal device consists of two transparent plates, 3 and 4, for example made from glass; in the case of an active matrix device these will usually be of aluminosilicate (alkali free) glass often with a passivation layer of $SiO_2$. For an active matrix display, the active devices, eg thin film transistors, are fabricated and the colour filter layer is added for a full colour display. These plates are coated on their internal face with transparent conducting electrodes 6 and 7, often Indium tin oxide (ITO) which is patterned using photolithography techniques.

The transparent plates 3 and 4 are coated with a photoactive sample, comprising one or more liquid crystal compounds according to the invention. A typical coating procedure involves the dissolution of one of the compounds of the invention in a solvent, for example cyclopentanone, followed by spin coating of the photoactive compound on the transparent plate. Once the photoactive compound has been coated onto the plates it is exposed to actinic radiation to induce cross-linking of the photoactive molecules. The cross-linking process can be monitored by measuring the birefringence of the alignment layer. The intersections between each column and row electrode form an x, y matrix of addressable elements or pixels. A spacer 5 e.g. of polymethyl methacrylate separates the glass plates 3 and 4 to a suitable distance e.g. 2-7 microns preferably 4-6 microns. Liquid crystal mixture 2 is introduced between glass plates 3,4 by filling the space in between them. This may be done by flow filling the cell using standard techniques. The spacer 5 is sealed with an adhesive in a vacuum using an existing technique. Polarisers 13 may be arranged in front of and behind the cell.

The device may operate in a transmissive or reflective mode (see FIGS. 2 and 3). In the former, light passing through the device, e.g. from a tungsten bulb, is selectively transmitted or blocked to form the desired display. In the reflective mode a mirror, or diffuse reflector (16), is placed behind the second polariser 13 to reflect ambient light back through the cell and two polarisers. By making the mirror partly reflecting, the device may be operated both in a transmissive and reflective mode.

The alignment layers (not shown) have two functions, one to align contacting liquid crystal molecules in a preferred direction, and the other to give a tilt to these molecules—a so called surface tilt—of a few degrees typically around 4° or 5°. In an alternative embodiment, a single polariser and dye mixture may be combined. Liquid crystal compounds of the current invention may also be used in LCDs with an actively addressed matrix e.g. thin film transistors (TFT-LCDs) or a passively addressed matrix e.g—, dual scan STN.

General Reaction Schemes

The following reaction schemes for producing novel liquid crystal compounds according to the present invention also form further aspects of the present invention.

Scheme 1

Scheme 1 shows the synthesis of precursors to compounds of Formula (XIX), where the ring systems are disposed on the opposite side to the acetal moiety.

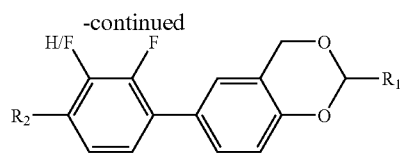

Scheme 1

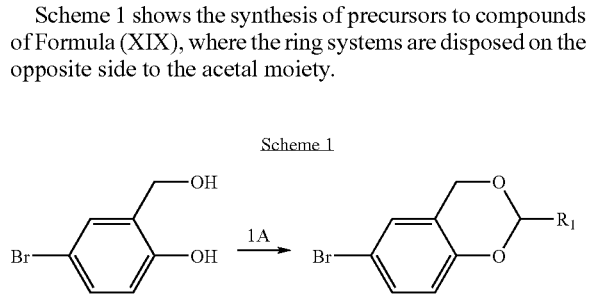

1A ... $R_1$CHO, PTSA, toluene
1B ... Pd(PPh3)4, Na2CO3, DME, water

The diol is a commercially available reagent, which can be condensed with the aldehyde containing the selected $R^1$ group, in the presence of para-toluensulfonic acid (PTSA) and toluene to generate the corresponding acetal.

The optionally fluorinated phenyl moiety contains the desired $R^2$ group and a boronic acid. The boronic acid was prepared according to standard methods in the public domain. The bromide of the dioxatetralin moiety is then coupled to the boronic acid via a Suzuki coupling reaction, in the presence of Pd(PPh$_3$), sodium carbonate, DME and water to produce the final product liquid crystal material in good yields.

Scheme 2

Scheme 2 shows, by way of example, the synthesis of 2(4'-alkylcyclohexyl)-6-bromobenzo[1,3]dioxane, and precursors to compounds of Formula (XX), in which compounds the dioxatetralin moiety is disposed between the ring systems.

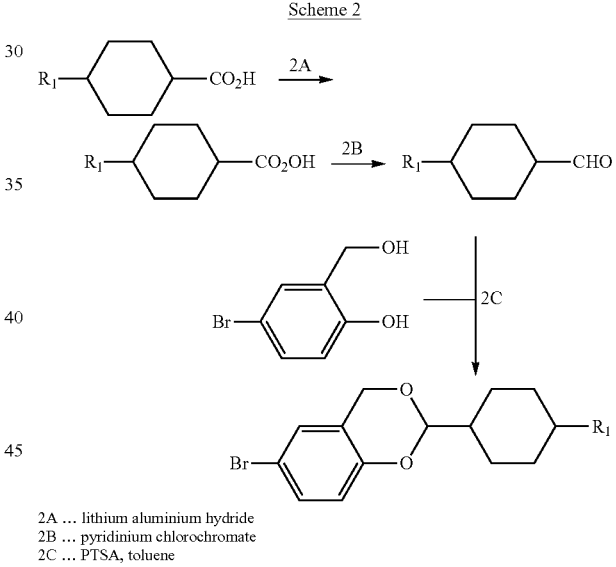

2A ... lithium aluminium hydride
2B ... pyridinium chlorochromate
2C ... PTSA, toluene The compounds were synthesised from the available trans-4-alkylcyclohexanecarboxylic acid. The acid was reduced to the alcohol with lithium aluminium hydride and the resulting alcohol selectively oxidised by pyridinium chlorochromate to the desired aldehyde. Condensation of the aldehyde with 5-bromo-2-hydroxybenzyl alcohol, under acidic conditions PTSA in toluene gave the 2(4'-alkylcyclohexyl)-6-bromobenzo[1,3]dioxane intermediate.

Compounds of Formula (XX) including (XV), where additional ring systems are present, may be prepared by a Suzuki coupling of the bromide with an appropriate arylboronic acid as detailed in Scheme 1 so as to furnish the desired product.

Scheme 3

Scheme 3 shows the synthesis of precursors to compounds of Formula (I), where fluorination of the dioxatetralin unit at $R^5$ is achieved.

Scheme 3

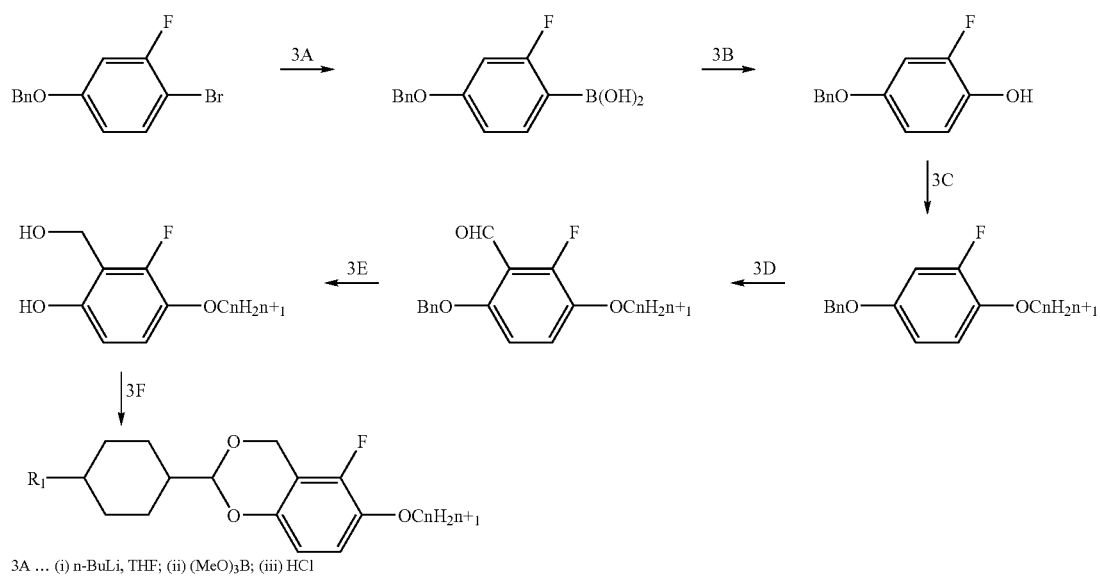

3A ... (i) n-BuLi, THF; (ii) (MeO)₃B; (iii) HCl
3B ... H₂O₂, ether
3C ... alkylBr, K₂CO₃, butanone
3D ... (i) n-BuLi, THF; (ii) DMF; (iii) NH₄Cl
3E ... H₂, Pd/C
3F ... PTSA, toluene The benzyl protected starting material is added to n-BuLi in THF at −78° C., B(OMe)₃ is then added to the resulting organometallic. The reaction is worked up under acid conditions to furnish the boronic acid. The boronic acid is oxidised to the alcohol using hydrogen-peroxide. A Williamson ether synthesis using the desired alkyl bromide ($BrC_nH_{2n+1}$) in the presence of potassium carbonate furnishes the desired ether. The next step is removal of the acidic proton, the ether is added to n-BuLi in THF at −78° C., and the resulting anion quenched with DMF, the reaction is worked up in ammonium chloride to generate the corresponding aldehyde. Reduction of the aldehyde and debenzylation is achieved by reaction with palladium on activated charcoal in the presence of hydrogen, which furnishes the benzyl diol. Condensation of the diol with the aldehyde $R^1CHO$, produces the acetal in the same fashion as described in scheme 1.

Scheme 4

Scheme 4 shows the synthesis of precursors to compounds of Formula (I), where fluorination of the dioxatetralin unit at $R^3$ and/or $R^4$ is achieved.

Scheme 4

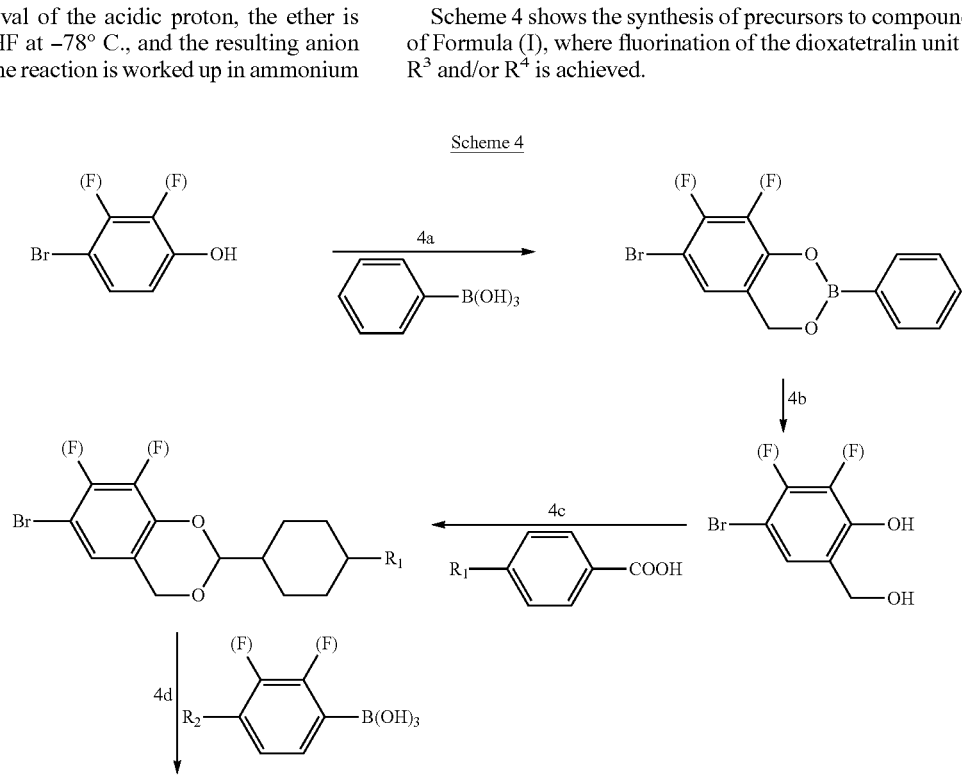

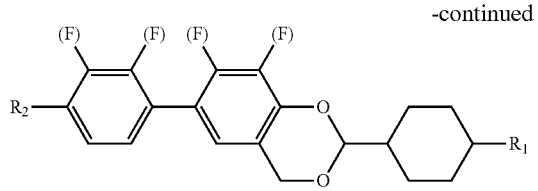

4a propanoic acid, paraformaldehyde, toluene
4b H₂O₂, THF
4c PTSA, DCM
4d Pd(PPh₃)₄, Na₂CO₃, H₂O, DME The optionally fluorinated, bromophenol is reacted with paraformaldehyde under acidic conditions to yield the aldehyde ortho to the hydroxy group. Reaction of the aldehyde and the phenol with a boronic acid furnishes the boronic acid ester, which is oxidatively cleaved by hydrogen peroxide to furnish the diol. The diol may be reacted with a suitable carboxylic acid $R^1COOH$, containing the desired $R^1$ group, under acidic conditions of PTSA, to produce the corresponding acetal.

Finally a Suzuki coupling of the bromide with an appropriate arylboronic acid, comprising the desired ring system and $R^2$ terminal end group, may be carried out as detailed in Scheme 1, so as to furnish the desired product.

The above scheme for introducing halogen substitution of the dioxatetralin moiety at any of $R^3$, $R^4$ and $R^5$ forms a further aspect of the invention.

It is within the scope of the invention that you could also prepare compounds made using Scheme 3, by this method, by starting from 3-bromo-2-fluorophenol.

Specific Example of the Synthesis of RK287

By way of example only, a preferred method for synthesising a difluorinated, 2 ring liquid crystal compounds according to the present invention, namely RK287, as below, is now described. The synthesis is based on Scheme 1, above but includes details of the initial preparation of the boronic acid, as well as other minor experimental modifications.

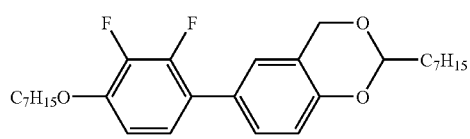

2,3-difluorophenol (50 g, 0.384 mol), 1-bromoheptane (75.6 g, 0.422 mol), K₂CO₃ (53.1 g, 0.384 mol) and butanone (400) are heated together under reflux overnight. Upon completion, the inorganic salts are filtered off and the solvent is removed in vacuum after extraction with Et₂O). The heptyl ether product is purified by vacuum distillation (105-115° C./0.5 mm Hg). Yield 85 g (97%).

nbutyl Lithium (2.5 in Hexane, 148 mL, 0.370 mol) is added dropwise to a stirred cooled (−78° C.) solution of the heptyl ether (84 g, 0.370 mol) in dry THF (400 mL) under an atmosphere of dry nitrogen. The reaction mixture is stirred (2.5 h) then a previously cooled (−78° C.) solution of B(OMe)₃ (57.7 g, 0.555 mol) in dry THF (100 mL) is added dropwise at −78° C. The reaction mixture is allowed to warm to room temperature overnight, and then stirred (1 hour) with HCl dilute (18.5%, 200 mL). The product is extracted into Et₂O and the combined extracted solution is washed with water and brine, and dried with MgSO₄. The solvent is removed in vacuum to yield the boronic acid. Yield 96 g (96%).

3-Bromo-2-hydroxybenzylalcohol (4.0 g, 12.77 mmol) is dissolved in DME (100 mL) and in 50 mL of an aqueous solution of Na₂CO₃ (15 g, 141.5 mmol). The solution is evacuated and flushed with an atmosphere of dry nitrogen. The catalyst Pd(PPh₃)₄ (0.5 g, 0.43 mmol) is added and the boronic acid (4.17 g, 15.32 mol) in DME (100 mL) is added dropwise. The reaction is heated under reflux (12 h) and under an atmosphere of dry nitrogen. Then the cooled reaction mixture is extracted into Et₂O and washed with water and brine, and dried with MgSO₄. The drying agent is filtered off and the solvent is removed in vacuum. The product RK287 is purified by column chromatography on silica (Hexane) and recrystallized from ethanol. Yield 4.8 g (81%).

EXAMPLES

The Examples below detail selected compounds and mixtures according to the invention, as prepared by the Applicant, as well as their properties and suitability for use in liquid crystal devices.

Example 1

A selection of 2 and 3 ring system compounds were synthesised with a range of alkyl/alkoxy end groups as tabulated below. In these compounds, the 2 and 3 rings are disposed on the phenyl ring portion of the dioxatetralin moiety. The compounds were synthesised using Scheme 1 above, but with an appropriately modified boronic acid reagent.

TABLE 3
selected 3 ring systems
| Compound number | Formula | R² | R¹ | Phase transitions (° C.) |
|---|---|---|---|---|
| RK201 | 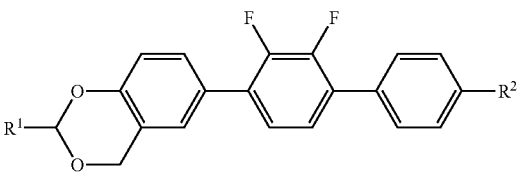 | C₅H₁₁ | C₃H₇ | K 75.8 SmA 126.1 N 172.1 I |
| RK202 | 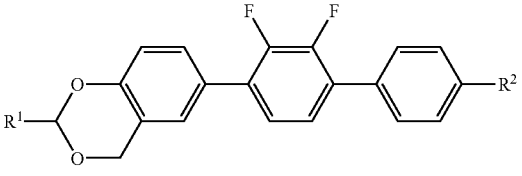 | C₅H₁₁ | C₇H₁₅ | K 64.7 SmA 144.3 N 156.4 I |
| RK203 | 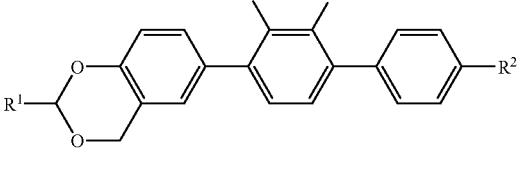 | C₅H₁₁ | C₅H₁₁ | K 55.9 SmA 145.3 N 165.2 I |
| RK208 | 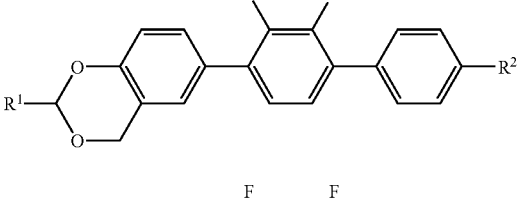 | C₃H₇ | C₇H₁₅ | K 63.7 SmA 133.0 N 161.5 I |
| RK215 | 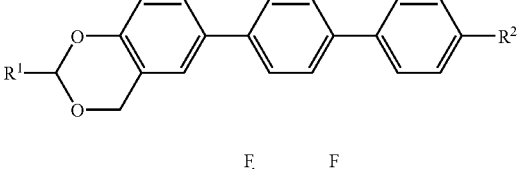 | C₃H₇ | C₅H₁₁ | K 76.1 SmA 126.1 N 174.6 I |
| RK216 | 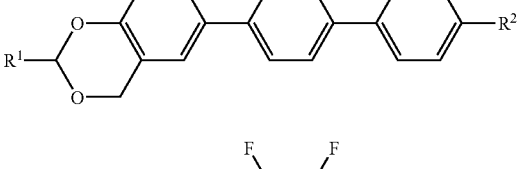 | C₃H₇ | C₃H₇ | K 80.9 N 185.8 I |
| RK217 | 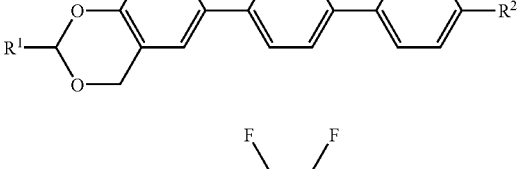 | C₇H₁₅ | C₅H₁₁ | K 71.7 SmA 179.6 N 183.9 I |
| RK218 | 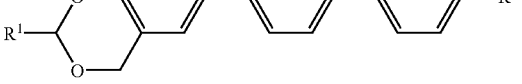 | C₇H₁₅ | C₇H₁₅ | K 72.5 SmA 178.5 I |

TABLE 3-continued selected 3 ring systems

| Compound number | Formula | $R^2$ | $R^1$ | Phase transitions (° C.) |
|---|---|---|---|---|
| RK219 | (structure) | $C_7H_{15}$ | $C_7H_{15}$ | K 128.4 SmA 197.3 I |
| RK220 | (structure) | $C_5H_{11}$ | $C_7H_{15}$ | K 134.9 SmA 204.0 I |
| RK221 | (structure) | $C_7H_{15}$ | $C_5H_{11}$ | K 132.5 SmA 195.5 I |
| RK222 | (structure) | $C_5H_{11}$ | $C_5H_{11}$ | K 137.9 SmA 205.1 I |

TABLE 8 selected 2 ring systems

| Compound number | Formula | $R^2$ | $R^1$ | Phase transitions (° C.) |
|---|---|---|---|---|
| RK241 | (structure) | $C_4H_9O$ | $C_5H_{11}$ | K 45.4 N 56.8 I |

In Table 3 and Table 8, $R^3$, $R^4$ and $R^5$ are hydrogen and $X^1$ and $X^2$ (where present) are direct bonds. A selection of the above compounds were subjected to a variety of tests to ascertain their physical properties as follows:

Optical Properties

The homologue with the lowest melting point of all these compounds was identified as RK203 and this was dissolved in a host material 20-113, (a commercially available low delta epsilon mixture), at 20% and 40% dopant levels.

This mixture was then tested for its phase transition characteristics as recorded in Tables 3 and 8, by placing the material in a standard test cell and observing it through a microscope as it was heated and cooled.

The same was done for the two ring system RK241. The birefringence was measured using an Abbé refractometer, the liquid crystal mixture was aligned using PVA or lecithin as required, and the results extrapolated to 100% of the dopant.

The following was observed:

TABLE 4

Birefringence data

| Dopant | Conc (wt %) | Δn 60° C. | Δn 40° C. | Δn 25° C. | Ext Δn 25° C. |
|---|---|---|---|---|---|
| RK241 | 40 | 0.0981 | 0.1113 | 0.1173 | 0.147 |
|  | 20 | 0.0939 | 0.1028 | 0.1081 |  |
| RK203 | 19.99 | 0.1109 | 0.1175 | 0.1211 | 0.2237 |
|  | 39.25* | 0.1335 | 0.1406 | 0.1458 |  |

*Denotes that dopant dropped out of solution overnight

These materials exhibit relatively high birefringence due to their linear conjugated structures and the number of conjugated aromatic rings.

Thermal Properties

A representative host mixture was formulated from the dioxatetralins to provide a nematic phase containing 100% of the novel compounds and to establish their mutual miscibility. This is simply formulated as a mixture of three representative homologues without any attempt to optimise the mixture as a eutectic:

| | |
|---|---|
| RK216 | 30% |
| RK208 | 30% |
| Rk203 | 40% |

The following phase behaviour was observed:
K 38.9 SmA 124.6 N 169.1 I

Dielectric Studies

The permittivities of the material in nematic solutions have also been studied and the following was obtained:

TABLE 5

The permittivities of the dioxatetralin material in solution and extrapolated to 100% doping levels.

| Mixture | $\epsilon_\parallel$ | $\epsilon_\perp$ | $\Delta\epsilon$ | Extrapolated $\Delta\epsilon$ |
|---|---|---|---|---|
| 20-113 | 2.66 | 2.63 | 0.03 | — |
| 20-113 plus 40% RK241 | 3.74 | 3.58 | 0.24 | 0.525 (+ve) |
| 20-113 plus 20% RK203 | 2.86 | 3.16 | −0.3 | −1.65 |

In these materials a single fluoro substituent gives rise to positive dielectric anisotropy whereas the use of two (or more) fluoro substituents gives rise to a nematic phase exhibiting negative dielectric anisotropy.

Electro-Optical Studies

The nematic materials that were produced above, by doping RK241 and RK203 respectively into 20-113 at levels of 40% and 20%, were used in this study. These materials were used to fill cells that had been prepared using a homeotropic alignment agent, for RK203 and a planar alignment layer for RK241. These cells were then observed on a microscope through crossed polarisers; the optical extinction observed between crossed polarisers verifies that homeotropic alignment had been achieved for the mixture containing RK203. The cells were subsequently tested in voltage induced birefringence mode, firstly to examine the form of the static switching curve and establish the switching threshold voltage, and secondly to scope the switching time of the materials. It must be emphasised that these results for RK203 were obtained in homeotropic cells without any controlled pretilt, and in both cases no optimisation of the cell or optical configuration has been attempted. The tests were carried out solely on the 20% doped material RK203.

The electro-optical response of a 7.55 μm thick device filled with a mix of 20% RK203 in 20-113 host material, gave rise to an observed threshold voltage of ca. 17V.

TABLE 6

Electro-optical response of 20% RK203 doped into 20-113.

| Mix | Cell thickness (μm) | $\epsilon_\parallel$ | On (ms) Delay | On (ms) Switch | Off (ms) Delay | Off (ms) Switch |
|---|---|---|---|---|---|---|
| 20-113 plus 40% RK241 | 9.10 (NB planar) | 3.74 | 48 | 232 | 28 | 276 |
| 20-113 plus 20% RK203 | 7.55 | 2.86 | 100 | 240 | 28 | 45 |

RK203 shows a relatively fast response when switching off but a rather slow switch on time, mainly because of the low delta epsilon. This device was switched between 0 v and 22 volts RMS. The threshold voltages are in all cases high, which is to be expected under these un-optimised conditions and using a dilute solution in a substantially zero anisotropy host.

In all cases, lateral fluorination is applied to increase the dielectric constant perpendicular to the molecular long axis. A further series of compounds to compare the effect of mono and di fluorination of the rings were similarly synthesised and evaluated.

Example 2

Mono-Fluorinated Compounds

A series of 4-alkoxy-2-fluorophenyl derivatives shown in Table 7 were synthesised. The melting points are generally quite low and the compounds tend to exhibit nematic phases with some underlying smectic tendencies.

TABLE 7

Monofluorophenyl substituted dioxatetralin LC's.

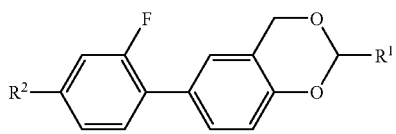

| Compound | R² | R¹ | Phase behaviour |
| --- | --- | --- | --- |
| RK232 | C₄H₉O | C₃H₇ | K 66.3 (N 48.1) I |
| RK241 | C₄H₉O | C₅H₁₁ | K 45.4 N 56.8 I |
| RK285 | C₄H₉O | C₇H₁₅ | K 42.6 SmA 53.4 N 57.9 I |
| RK269 | C₆H₁₃O | C₃H₇ | K 28 N 52.9 I |
| RK268 | C₆H₁₃O | C₅H₁₁ | K 34.4 SmA 41.3 N 58.0 I |
| RK300 | C₈H₁₇O | C₃H₇ | K 44.3 N 58.9 I |

The physical properties of the compounds were determined at 20% concentration in the host system 20-113. The phase behaviour was determined by optical microscopy using a polarising microscope and a Mettler FP82 hot-stage and controller. Refractive indices and birefringence were measured using an Abbé refractometer at 25, 40 and 60° C. and dielectric constants measured in planar ($SiO_x$ or Nissan SE130) and homeotropic (chrome complex) cells using a Hewlett Packard LCR meter at 25° C. Where it was not possible to dissolve 20% of the compound under test into the host, a 10% concentration was tried instead. In some cases 40% concentration of the compound under test was also used. The results are shown in Table 9. Table 10 shows the variation in birefringence and refractive indices with temperature for the 3 compounds under test.

The monofluorophenyl compounds are generally slightly positive $\Delta\epsilon$ materials, with higher values of both E parallel and E perpendicular than the host mixture. In the case of RK285 the dielectric anisotropy is almost zero. Birefringence of the mixtures is higher than that of the host, and is as expected for a 2 aromatic ring system.

The mixtures were filled into an antiparallel aligned (Frederiks) cell with rubbed SE180 polymer surfaces giving planar alignment as the mixtures had positive dielectric anisotropy. A 1 kHz square wave was applied for a period of 0.5 to 1 s and then turned off and the relaxation time of the cell was followed. The cell was placed in a microscope with a ×4 objective lens. Illumination was provided by a dc stabilised white light source with a laser notch filter to provide light of 589.0 nm and the response detected with a large area fast responding (<1 μs) photodiode. The rotational viscosity and relaxation time of the mixtures was determined by a fit of the optical response to the theoretical equations.

The very low dielectric anisotropy of these mixtures means that switching occurs at between 20 and 25 V, using this measurement method the cell thickness did not need to be optimised for $\Delta$nd. The switching behaviour of the host 20-113 was also determined.

TABLE 9

The physical properties of mixtures of the monofluorophenyl substituted dioxatetralins measured in 20-113.

| Mix No | Compound | Conc. in 20-113 (wt %) | Transitions | $\Delta$n 25° C. | $\epsilon_\parallel$ | $\Delta\epsilon$ | Extrapolated $\Delta\epsilon$ |
| --- | --- | --- | --- | --- | --- | --- | --- |
| — | 20-113 | | | 0.0984 | 2.66 | 0.03 | |
| VM622 | RK300 | 19.4 | N 89.9-92.3 I | 0.1066 | 3.116 | +0.112 | +0.29 |
| VM614 | RK268 | 19.7 | N 90.9-93.3 I | 0.1064 | 3.124 | +0.119 | +0.3 |
| VM617 | RK268 | 40.2 | N 81.5-82.7 I | 0.1142 | 3.653 | +0.184 | +0.3 |
| VM620 | RK285 | 20.2 | N 90.8-92.7 I | 0.1059 | 3.083 | +0.071 | 0.07 |

TABLE 10

The birefringence and refractive indices at various temperatures.

| Mixture | Temperature ° C. | $n_e$ | $n_o$ | $\Delta$n |
| --- | --- | --- | --- | --- |
| VM622 | 60 | 1.5797 | 1.4872 | 0.0925 |
| | 45 | 1.5933 | 1.4920 | 0.1013 |
| | 25 | 1.6025 | 1.4959 | 0.1066 |
| VM614 | 60 | 1.5794 | 1.4869 | 0.0925 |
| | 40 | 1.5927 | 1.4914 | 0.1013 |
| | 25 | 1.6024 | 1.4959 | 0.1064 |
| VM617 | 60 | 1.5854 | 1.4888 | 0.0966 |
| | 40 | 1.6011 | 1.4925 | 0.1086 |
| | 25 | 1.6096 | 1.4954 | 0.1142 |
| VM620 | 60 | 1.5797 | 1.4876 | 0.0921 |
| | 40 | 1.5931 | 1.4919 | 0.1012 |
| | 25 | 1.6020 | 1.4961 | 0.1059 |

TABLE 11

Switching behaviour of mixtures in 8-9 micron planar aligned cells.

| Mixture | $\Delta\epsilon$ | Vth | d (μm) | Rot visc MPa · s | Relaxation time (ms) |
| --- | --- | --- | --- | --- | --- |
| 20-113 | 0.03 | 38 | 8.55 | 128.4 | 37.2 |
| VM622 | 0.112 | 11.1 | 9.2 | 111.4 | 77.2 |

TABLE 11-continued

Switching behaviour of mixtures in 8-9 micron planar aligned cells.

| Mixture | Δε | Vth | d (μm) | Rot visc MPa·s | Relaxation time (ms) |
|---|---|---|---|---|---|
| VM614 | 0.119 | 12.8 | 9.75 | 160 | 88 |
| VM617 | 0.184 | 9.2 | 8.52 | 220 | 115.8 |
| VM620 | 0.071 | 12.8 | 8.86 | 104 | 75.8 |

Example 3

Di-Fluorinated Compounds

A number of compounds have also been synthesised with 2 fluoro substituents. The physical properties of the compounds in a mixture with 20-113 were determined and the results are shown in Tables 12 and 13.

TABLE 12

The phase behaviour of some alkyl and alkoxydifluorophenyl substituted dioxatetralins.

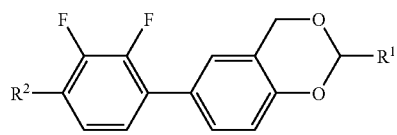

| Compound | R$_2$ | R$_1$ | Phase behaviour |
|---|---|---|---|
| RK329 | C$_3$H$_7$O | C$_5$H$_{11}$ | K 65.4 I |
| RK238 | C$_4$H$_9$O | C$_3$H$_7$ | K 59.1 I |
| RK240 | | C$_5$H$_{11}$ | K 75.2 I |
| RK256 | C$_5$H$_{11}$ | C$_5$H$_{11}$ | K 37.1 I |
| RK289 | | C$_7$H$_{15}$ | K 37.8 (SmA 17.6) I |
| RK284 | | C$_3$H$_7$ | K 33.2 (SmA –12.7 N 2.9) I |
| RK286 | C$_7$H$_{15}$ | C$_5$H$_{11}$ | K 19.1 I |
| RK287 | C$_7$H$_{15}$O | C$_7$H$_{15}$ | K 70 SmA 77.3 I |

TABLE 13

The physical properties of mixtures containing various concentrations of alkyl di-fluorophenyl-dioxatetralins.

| Mix No | Compound | Conc. in 20-113 (wt %) | Transitions | Δn 25° C. | ε∥ | Δε | Extrapolated Δε |
|---|---|---|---|---|---|---|---|
| — | 20-113 | | | 0.0984 | 2.66 | 0.03 | |
| VM621 | RK286 | 20.05 | N 82.4-85.7 I | 0.1027 | 2.841 | –0.355 | –2 |
| VM615 | RK284 | 20.04 | N 81.9-84.8 I | 0.1039 | 2.83 | –0.428 | –2.4 |
| VM618 | RK284 | 40.14 | N 61.6-65.3 I | 0.1068 | 3.137 | –0.892 | –2.4 |
| VM616 | RK289 | 20.26 | N 79.8-84.2 I | 0.1012 | 2.870 | –0.307 | –1.8 |
| VM619 | RK289 | 40.0 | N 63.5-66.2 I | 0.1036 | 2.856 | –0.957 | –2.5 |

The difluorinated compounds are negative Δε materials, the value ranges from –1.8 to –2.5, extrapolated from mixtures in 20-113. The birefringence of the mixtures remains at about 0.1 which is as expected for these compounds. The birefringence values as a function of temperature are shown in Table 14, below.

TABLE 14

The birefringence and refractive indices at 25, 40 and 60° C. of alkyl di-fluorophenyl-dioxatetralins in 20-113.

| Mixture | Temperature (° C.) | n$_e$ | n$_o$ | Δn |
|---|---|---|---|---|
| VM621 | 60 | 1.5738 | 1.4868 | 0.0870 |
| | 40 | 1.5880 | 1.4909 | 0.0971 |
| | 25 | 1.5975 | 1.4948 | 0.1027 |
| VM616 | 60 | 1.5726 | 1.4871 | 0.0854 |
| | 40 | 1.5862 | 1.4912 | 0.0950 |
| | 25 | 1.5961 | 1.4949 | 0.1012 |
| VM619 | 60 | 1.5618 | 1.4952 | 0.0656 |
| | 40 | 1.5858 | 1.4919 | 0.0940 |
| | 25 | 1.5984 | 1.4948 | 0.1036 |
| VM615 | 60 | 1.5743 | 1.4873 | 0.0870 |
| | 40 | 1.5896 | 1.4920 | 0.0976 |
| | 25 | 1.5990 | 1.4950 | 0.1039 |
| VM618 | 60 | 1.5679 | 1.4927 | 0.0752 |
| | 40 | 1.5896 | 1.4937 | 0.0959 |
| | 25 | 1.6024 | 1.4956 | 0.1068 |

The switching characteristics of the mixtures in chrome complex (homeotropic alignment) cells of ~8 micron thickness was determined. Table 15, below, gives the response speed of the mixture. The difluorinated materials have a much larger magnitude of dielectric anisotropy than the monofluorinated materials and this is reflected in the reduced threshold voltages which are typically close to 5V. This change is of course in addition to the alteration of the sign of the dielectric anisotropy from positive to negative. The mixtures all have a respectable negative dielectric anisotropy so switching voltages are lower than the host material, switching times and viscosities are good with some dependence on the concentration of the dopant as would be expected.

TABLE 15

Switching behaviour of mixtures in 8 micron homeotropically aligned cells.

| Mixture | Δε | Vth | d (μm) | Rot visc MPa·s | Relaxation time (ms) |
|---|---|---|---|---|---|
| 20-113 | 0.03 | 38 | 8.55 | 128.4 | 37.2 |
| VM621 | −0.355 | 6.7 | 8.98 | 110.8 | 63.2 |
| VM616 | −0.307 | 7.1 | 9.39 | 97 | 62.4 |
| VM619 | −0.957 | 3.9 | 9.24 | 154.6 | 102.4 |
| VM615 | −0.428 | 6.54 | 7.94 | 129.2 | 50.2 |
| VM618 | −0.892 | 4.2 | 8.97 | 179 | 103.4 |

Example 4

3-Ring Difluorinated Biphenyl Compounds

In these compounds, ring systems are disposed either side of the dioxatetralin unit and may be synthesised using Scheme 2 (+Scheme 1). The phase behaviour and structure of a number of such compounds is shown in Table 16.

TABLE 16

3-ring systems, where the dioxatetralin is substituted on both sides and is in the centre of the LC chain.

| Compound | structure | Phase behaviour |
|---|---|---|
| RK357 | $C_5H_{11}$—[3,2-F,F-phenyl]—[dioxatetralin]—[phenyl]—$OC_2H_5$ | K 114.1 N 155.6 I |
| RK360 | $C_5H_{11}$—[phenyl]—[dioxatetralin]—[2,3-F,F-phenyl]—$OC_2H_5$ | K 109.8 (SmA 105.2) N 157.7-159.2 I |
| RK361 | $C_5H_{11}$—[3,2-F,F-phenyl]—[dioxatetralin]—[2,3-F,F-phenyl]—$OC_2H_5$ | K 102 N 115.7-118.1 I |

The physical properties of mixtures of 20-113 and the compounds were again determined and are shown in Table 17. Compound RK360 was only soluble at 10% instead of the normal 20% used for the physical measurement studies. The compounds exhibited negative dielectric anisotropy as well as birefringence values typical of compounds containing 3 aromatic rings.

TABLE 17

Physical properties of the mixtures containing the 3-ring compounds.

| Mix No | Ref. No | Conc. in 20-213 (wt %) | Transitions (° C.) | Δn 25° C. | $\epsilon_{\parallel}$ | Δε | Extrapolated Δε |
|---|---|---|---|---|---|---|---|
| VM630 | RK360 | 19.99 | Insoluble | | | | |
| VM631 | RK360 | 9.97 | N 105.4-107.5 I | 0.108 | 2.618 | −0.347 | −3.7 |
| VM632 | RK361 | 20.02 | N 102.2-105.1 I | 0.113 | 3.109 | −0.591 | −3 |

The extrapolated negative dielectric anisotropy for compounds RK361 and RK360 of −3 and −3.7 compare well with the value of compound RK203 (reported above), which had $\Delta\varepsilon$ of −1.6.

The switching behaviour of the two mixtures VM631 and VM632 was determined and is shown in Table 18.

viscosity than the analogous phenyl containing compounds as well as increased stability for long term use in display applications.

The following compounds shown in Table 19 were synthesised from the available trans-4-alkylcyclohexanecarboxylic acid, using Scheme 2 and Scheme 1 above.

TABLE 19

The phase behaviour and structure of some cyclohexyl compounds.

| Compound | Structure | Phase behaviour |
|---|---|---|
| RK331 | $C_5H_{11}$—[phenyl]—[dioxane-fused phenyl]—[cyclohexyl]—$C_5H_{11}$ | K 144.4 SmA 182.7-187.2 I |
| RK354 | $C_8H_{17}O$—[2-F-phenyl]—[dioxane-fused phenyl]—[cyclohexyl]—$C_5H_{11}$ | K 70.9 (SmC 68.1) SmA 120.7 N 161.9 I |
| RK368 | $C_3H_7O$—[2-F-phenyl]—[dioxane-fused phenyl]—[cyclohexyl]—$C_3H_7$ | K 80.9 N 180-181.5 I |
| RK348 | $C_3H_7O$—[2,3-diF-phenyl]—[dioxane-fused phenyl]—[cyclohexyl]—$C_3H_7$ | K 109.4 SmA 131.3 N 183.5 I |
| RK349 | $C_5H_{11}$—[2,3-diF-phenyl]—[dioxane-fused phenyl]—[cyclohexyl]—$C_3H_7$ | K 54.9 SmA 123.0 N 147.8 I |
| RK325 | $C_5H_{11}$—[2,3-diF-phenyl]—[dioxane-fused phenyl]—[cyclohexyl]—$C_5H_{11}$ | K 56.2 SmA 135-142 N 145 I |

TABLE 18

Response times of the mixtures VM631 and VM632.

| Mixture | $\Delta\varepsilon$ | Vth | d (µm) | Rot visc MPa·s | Relaxation time (ms) |
|---|---|---|---|---|---|
| 20-113 | 0.03 | 38 | 8.55 | 128.4 | 37.2 |
| VM631 | −0.347 | 11.3 | 7.74 | 324 | 49.4 |
| VM632 | −0.591 | 8.4 | 8.22 | 270 | 57.4 |

Example 5

Cyclohexyl Dioxatetralins

Advantageously it has been found that the aromatic rings such as 1,4-phenylene may be substituted by cycloalkyl rings, preferably cyclohexyl. Compounds where the phenyl was replaced by cyclohexyl may lead to a lower birefringence and The non-fluorinated compound RK331 exhibits only a smectic A phase. All of the other compounds contain one or more fluorine atoms and exhibit a nematic phase as well as a smectic phase. The shorter terminal alkyl/alkoxy chains on RK368 compared to RK354 increase the melting and clearing points and have suppressed the smectic phase behaviour when 1 fluorine atom is present. When 2 fluorine atoms are present the alkoxy and alkyl substituted compounds RK325, RK348 and RK349 all exhibit a smectic A phase as well as a nematic phase. The melting points of the 2 alkyl homologues RK325 and RK349 are low for the size of the molecule.

The physical properties of the compounds in mixtures with 20-113 were determined using the techniques described earlier and the results are shown in Tables 20 and 21. As found above, the monofluorinated compounds exhibit a low positive $\Delta\varepsilon$ while the difluorinated compounds are negative $\Delta\varepsilon$ materials. The extrapolated $\Delta\varepsilon$ ranges from +0.4 to +0.9 for the monofluorinated compounds and −1.6 to −3.5 for the difluorinated compounds; these are similar values to the phenyl compounds discussed earlier.

The switching behaviour of the mixtures in 8 micron cells was determined and the results are given in Table 22.

TABLE 20

Assessment of the physical properties of the cyclohexyl compounds.

| Mix No | Ref. No | Conc in 20-113 (wt %) | Transitions (° C.) | Δn 25° C. | ε∥ | Δε | Extrapolated Δε |
|---|---|---|---|---|---|---|---|
| VM627 | RK331 | 19.94 | N 116.7-118.9 I | 0.109 | 2.855 | +0.099 | 0.37 |
| VM634 | RK368 | 19.85 | N 115.9-118.3 I | 0.111 | 3.202 | +0.208 | 0.92 |
| VM624 | RK354 | 19.89 | N 114.8-16.2 I | 0.108 | 3.062 | +0.145 | 0.6 |
| VM625 | RK349 | 20.08 | N 109.9-12.6 I | 0.108 | 2.873 | −0.302 | −1.6 |
| VM626 | RK348 | 19.95 | N 115.5-18.1 I | 0.110 | 3.119 | −0.671 | −3.5 |
| VM629 | RK325 | 20.09 | N 109.7-11.9 I | 0.107 | 2.717 | −0.386 | −2 |

TABLE 21

The birefringence and refractive indices for mixtures containing a cyclohexyl unit.

| Mixture | Temperature | $n_e$ | $n_o$ | Δn |
|---|---|---|---|---|
| VM627 | 60 | 1.5873 | 1.4885 | 0.099 |
|  | 50 | 1.5988 | 1.4936 | 0.105 |
|  | 25 | 1.6071 | 1.4977 | 0.109 |
| VM634 | 60 | 1.5881 | 1.4878 | 0.1003 |
|  | 40 | 1.5994 | 1.4931 | 0.1063 |
|  | 25 | 1.6089 | 1.4979 | 0.111 |
| VM624 | 60 | 1.5851 | 1.4866 | 0.099 |
|  | 40 | 1.5959 | 1.4917 | 0.104 |
|  | 25 | 1.6040 | 1.4960 | 0.108 |
| VM625 | 60 | 1.5836 | 1.4868 | 0.097 |
|  | 40 | 1.5957 | 1.4917 | 0.104 |
|  | 25 | 1.6035 | 1.4960 | 0.108 |
| VM626 | 60 | 1.5879 | 1.4870 | 0.101 |
|  | 40 | 1.5977 | 1.4917 | 0.106 |
|  | 25 | 1.6054 | 14959 | 0.110 |
| VM629 | 60 | 1.5828 | 1.4863 | 0.0966 |
|  | 40 | 1.5944 | 1.4917 | 0.1028 |
|  | 25 | 1.6029 | 1.4958 | 0.1071 |

TABLE 22

Switching speeds of the mixtures containing a cyclohexyl unit.

| Mixture | Δε | Vth | d (μm) | Rot visc MPa·s | Relaxation time (ms) |
|---|---|---|---|---|---|
| 20-113 | 0.03 | 38 | 8.55 | 128.4 | 37.2 |
| VM627 | 0.099 | 27.5 | 8.75 | 1108 | 128 |
| VM634 | 0.208 | 11.9 | 8.67 | 276 | 79.6 |
| VM624 | 0.145 | 14.73 | 8.86 | 304 | 86 |
| VM625 | −0.302 | 7.6 | 8.81 | 112.6 | 66.6 |
| VM626 | −0.671 | 5.3 | 8.41 | 114 | 48.4 |
| VM629 | −0.386 | 7.8 | 8.38 | 203.6 | 68.6 |

Compounds VM627 to VM624 are again positive Δε mixtures and show good switching behaviour.

The negative Δε mixtures VM625 to VM629 were generally faster at switching than the monofluoro compounds, with the mixture containing the compound with the shortest end chain, VM626, being the fastest.

Example 6

Fluorination of the Dioxatetralin Ring

Fluorination directly of the dioxatetralin ring has the advantage that the fluorine atom(s) are locked in position relative to the oxygens of the dioxatetralin moiety. Schemes 3 and 4, above are suitable routes for preparing such compounds.

The presence of a fluorine at the $R^3$ position allows interaction between the fluorine and the oxygen from the dioxatetralin moiety.

The following compound shown in Table 23 was prepared.

TABLE 23

The phase behaviour and structure of the fluorinated dioxatetralin ring compounds.

| Compound | Structure | Phase behaviour |
|---|---|---|
| RK350 | C₃H₇O—[2-F-phenyl]—[F-phenyl-dioxane]—cyclohexyl—C₃H₇ | K-98.3-N-166.7-167.6-I |

The mono fluorinated dioxatetralin moiety, was incorporated into 20-113 as a 20% wt concentration. The physical properties of the mixture were assessed and are shown in Table 24, below.

TABLE 24

Assessment of the physical properties of a fluorinated dioxatetralin ring compound.

| Mix No | Ref. No | Conc in 20-113 (wt %) | Transitions (° C.) | Δn 25° C. | ε∥ | Δε |
|---|---|---|---|---|---|---|
| VM700 | RK350 | 20 | N 166.7-167.6-I | 0.110 | 3.6 | +0.3 |

TABLE 25

The birefringence and refractive indices for mixtures containing fluorinated dioxatetralin ring.

| Mixture | Temperature | $n_e$ | $n_o$ | Δn |
|---|---|---|---|---|
| VM700 | 25 | 1.607 | 1.497 | 0.110 |

This compound, although of positive dielectric anisotropy, shows good stability and good phase behaviour: smectic phases are absent in this compound.

Compounds of the invention are likewise of particular use in display devices using the in-plane switching effect. According to the disposition of in-plane electrodes relative to the local surface alignment direction of the liquid crystal, in plane switching modes may use nematic liquid crystals of either positive or negative dielectric anisotropy comprising compounds of the invention.

The compounds according to the invention, for example, may be used in twisted nematic, vertically aligned nematic, variable birefringence and/or in-plane switching devices which use surface alignment, relief features or patterned electrodes in such a way as to induce multiple domains in each pixel or cluster of pixels and so achieve improved uniformity, contrast or angle of view. Devices incorporating compounds or mixtures of the invention may be used in conjunction with optical components such as retardation films, lensatic films, diffusers and holographic films in order to achieve a chosen combination of contrast, viewing angle and colour balance.

A particular aim of the invention is to provide materials suitable for high quality displays using nematic or smectic liquid crystal layers on an active matrix backplane.

Further display modes in which the materials of the invention may be used include but are not limited to bistable nematic devices based upon switching between states which differ in twist by 180 degrees, bistable nematic devices based on surfaces which provide a plurality of preferred azimuthal alignment directions and bistable devices in which switching between high and low tilt states is accompanied by a substantial hysteresis. Compounds of the invention may be used in other devices including but not limited to reflective 45 degree twisted nematic displays, voltage controlled twist devices and hybrid transmissive/reflective nematic displays.

The invention claimed is:

1. A compound of Formula (I)

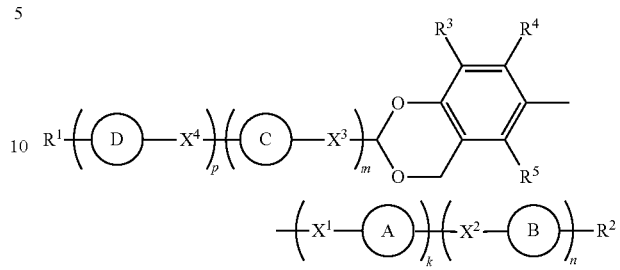

wherein $R^1$ and $R^2$ are independently selected from cyano, halo, optionally substituted hydrocarbyl, optionally substituted alkoxy, optionally substituted heterocyclyl, a group $R^{13}C(O)O$— or $R^{13}OC(O)$— where $R^{13}$ is optionally substituted hydrocarbyl;

$R^3$, $R^4$ and $R^5$ are independently selected from hydrogen, halogen, $CF_3$ or $SF_5$;

$X^1$, $X^2$, $X^3$ and $X^4$ are independently selected from a direct bond, —$CH_2CH_2$—, —$(CH_2)_4$—, —$CH_2O$—, —CH=CH—, —C≡C—, —COO—, —OCO—, or —$OCH_2$—;

and A, B, C and D are independently selected from a 1,4-phenylene, 1,4-cyclohexyl or a heterocyclic ring, any of which may be optionally substituted provided that at least one of rings C or D must be present;

and n is 0 or 1, m is 0 or 1, p is 0 or 1 and k is 0 or 1, provided that k+m+n+p is greater than 0, further provided that if k is 0 then n is 0, and also provided that if m is 0 then p is 0.

2. A compound according to claim 1 wherein both $R^1$ and $R^2$ are independently selected from alkyl or alkoxy.

3. A compound according to claim 2 wherein the alkyl or alkoxy groups have from 3 to 8 carbon atoms.

4. A compound according to claim 1 wherein $R^3$, $R^4$ and $R^5$ are selected from hydrogen or fluorine.

5. A compound according to claim 1 wherein $X^1$, $X^2$, $X^3$ and $X^4$ are selected from a direct bond or a group —$CH_2CH_2$—.

6. A compound according to claim 5 wherein $X^1$, $X^2$, $X^3$ and $X^4$ are direct bonds.

7. A compound according to claim 1 where k+m+n+p is 1 or 2.

8. A compound according to claim 1 wherein, when present each of rings A, B, C or D is substituted by at least one fluorine atom.

9. A compound according to claim 8 wherein there are 2 or more fluorine atoms present.

10. A compound according to claim 1 wherein A, B, C and D are selected from 1,4-phenylene, 1,4-cyclohexyl, 2,5-dioxanyl, pyridyl or 2,5-pyrimidinyl.

11. A compound according to claim 10 wherein A, B, C and D are selected from 1,4-phenylene or 1,4-cyclohexyl.

12. A compound according to claim 1, comprising a compound of Formula (XX)

(XX)

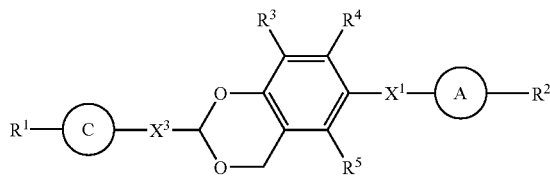

where $R^1, R^2, R^3, R^4, R^5, X^1, X^3$, A and C are as defined in claim 1.

13. A compound according to claim 12 wherein each of rings A and C are substituted by at least one fluorine atom.

14. A compound according to claim 12 wherein there are 2 or more fluorine atoms present.

15. A compound according to claim 12, comprising a compound of Formula (XV)

(XV)

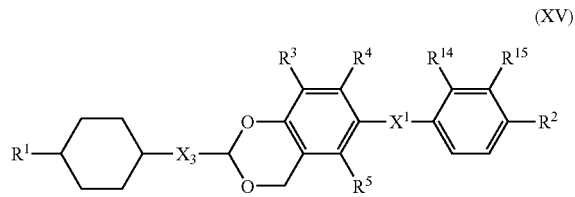

where $R^1, R^2, R^3, R^4, R^5, X^3$ and $X^1$ are as defined in claim 12, $R^{14}$ and $R^{15}$ are independently selected from hydrogen or halogen.

16. A compound according to claim 15 wherein one, two or three of $R^3, R^4, R^5, R^{14}$ and $R^{15}$ are fluorine and the others are hydrogen.

17. A compound according to claim 12, comprising a compound of Formula (XXV)

(XXV)

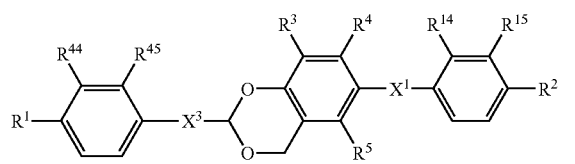

where $R^1, R^2, R^3, R^4, R^5, X^1$ and $X^3$ are as defined in claim 12, and $R^{14}, R^{15}, R^{44}$ and $R^{45}$ independently selected from hydrogen or halogen.

18. A compound according to claim 17 wherein one, two or three of $R^3, R^4, R^5, R^{14}$ and $R^{15}$ are fluorine and the others are hydrogen.

19. A compound according to claim 1, comprising a compound of Formula (XVIII)

(XVIII)

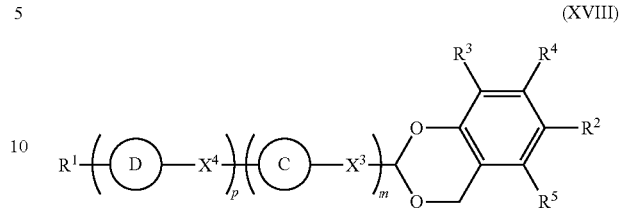

where p, m, $R^1, R^2, R^3, R^4, R^5, X^3, X^4$, C and D are as defined in claim 1.

20. A compound according to claim 19 wherein rings C or D are substituted by at least one fluorine atom.

21. A compound according to claim 20 wherein there are 2 or more fluorine atoms present.

22. A compound according to claim 19, comprising a compound of Formula (XXX)

(XXX)

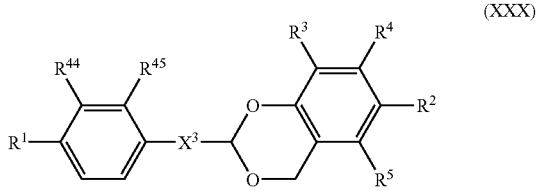

where $R^1, R^2, R^3, R^4, R^5$, and $X^3$ are as defined in claim 19, and $R^{44}$ and $R^{45}$ are independently selected from hydrogen or halogen.

23. A compound according to claim 22 wherein one, two or three of $R^3, R^4, R^5, R^{44}$ and $R^{45}$ are fluorine and the others are hydrogen.

24. A compound according to claim 19, comprising a compound of Formula (XXXV)

(XXXV)

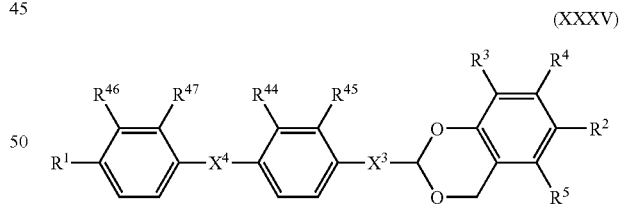

where $R^1, R^2, R^3, R^4, R^5, X^3$ and $X^4$ are as defined in claim 19, and $R^{44}, R^{45}, R^{46}$ and $R^{47}$ are independently selected from hydrogen or halogen.

25. A compound according to claim 24 wherein one, two or three of $R^3, R^4, R^5, R^{44}, R^{45}, R^{46}$ and $R^{47}$ are fluorine and the others are hydrogen.

26. A liquid crystal mixture comprising at least one compound according to claim 1.

27. A liquid crystal device comprising at least one compound according to claim 1.

28. A liquid crystal device comprising a liquid crystal mixture according to claim 26.

29. A device comprising two spaced cell walls each bearing electrode structures and treated on at least one facing surface with an alignment layer, a layer of a liquid crystal material enclosed between the cell walls, characterised in that it comprises at least one compound of claim 1.

30. A liquid crystal device according to claim 27, wherein the device is an Active Matrix Device, an STN device or a TN device.

31. A device according to claim 27, wherein the cell walls comprise at least 4 electrodes such as to allow said liquid crystal compound or mixture to be switched in at least two directions.

32. A method of preparing a device comprising at least one liquid crystal compound according to claim 1.

* * * * *